United States Patent [19]
Kmiec

[11] Patent Number: 5,731,181
[45] Date of Patent: *Mar. 24, 1998

[54] CHIMERIC MUTATIONAL VECTORS HAVING NON-NATURAL NUCLEOTIDES

[75] Inventor: Eric B. Kmiec, Malvern, Pa.

[73] Assignee: Thomas Jefferson University, Philadelphia, Pa.

[*] Notice: The term of this patent shall not extend beyond the expiration date of Pat. No. 5,565,350.

[21] Appl. No.: 664,487

[22] Filed: Jun. 17, 1996

[51] Int. Cl.$^6$ .................... C12N 15/00; C07H 21/00
[52] U.S. Cl. ..................... 435/172.3; 536/23.1
[58] Field of Search .............. 435/172.3, 240.2, 435/252.3, 254.11, 320.1; 536/320.1, 23.1, 25.3

[56] References Cited

U.S. PATENT DOCUMENTS

| | | | |
|---|---|---|---|
| 4,503,151 | 3/1985 | Paddock | 435/69.1 |
| 4,882,279 | 11/1989 | Cregg | 435/172.3 |
| 5,013,830 | 5/1991 | Ohtsuka et al. | 536/25.1 |
| 5,466,786 | 11/1995 | Buhr et al. | 536/26.26 |
| 5,565,350 | 10/1996 | Kmiec | 435/172.3 |
| 5,589,369 | 12/1996 | Seidman et al. | 435/172.3 |

OTHER PUBLICATIONS

Nielsen et al. Sequence–selective recognition of DNA by strand displacement with a thymine–substituted polyamide. Science vol. 254 1497–1500, 1991.

Lehninger Biochemistry, Second Edition Worth Publishers, Inc. 309–333 1975.

Shimizu et al., "Oligo(2'–O–methyl)ribonucleotides—Effective probes for duplex DNA", FEBS Letters 302:2, 155–158 (1992).

Monia et al., "Selective Inhibition of Mutant Ha–ras mRNA Expression by Antisense Oligonucleotides", J Biol Chem 267:28,19954–19962 (1992).

Roberts, R.W., & Crothers, D.M., "Stability and Properties of Double and Triple Helices: Dramatic Effects of RNA or DNA Backbone Compsition", Science 258:5087,1463–1466 (1992).

Monia et al., "Evaluation of 2'–Modified Oligonucleotides Containing 2'–Deoxy Gaps as Antisense Inhibitors of Gene Expression", J Biol Chem 268:19,14514–14522 (1993).

Lesnik et al., "Oligodeoxynucleotides Containing 2'–O–Modified Adenosine: Synthesis and Effect on Stability of DNA:RNA Duplexes", Biochemistry 32:7832–7838 (1993).

Shimizu et al., "Effects of 5-Methyl Substition in 2'–O–Methyloligo–(Pyrimidine) Nucleotides on Triple–Helix Formation", Bio & Med Chem Ltrs 4:8,1029–1032 (1994).

Kmiec et al., "The REC2 Gene Encodes the Homologous Pairing Protein of *Ustilago Maydis*", Mol. and Cell. Biol. 14:7163 (1994).

Yoon et al., "Targeted Gene Correction of Episomal DNA in Mammalian Cells Mediated by a Chimeric RNA–DNA Oligonucleotide", Proc. Natl. Acad. Sci. USA 93:2071 (Mar. 1996).

Hosono, K., et al., "Properties and Anti–HIV Activity of Hairpin Antisense Oligonucleotides Containing 2'–Methoxynucleosides with Base–Pairing in the Stem Region at the 3'-end", Antiviral Chemistry & Chemotherapy 7:86–93 (Mar. 1996).

*Primary Examiner*—James Ketter
*Assistant Examiner*—John S. Brusca
*Attorney, Agent, or Firm*—Daniel Hansburg

[57] ABSTRACT

The application concerns the design and use of small, duplex oligonucleotides and oligomers of nucleotide analogs, termed Chimeric Mutational Vectors (CMV) to effect mutation in a target gene of a eukaryotic cell by homologous recombination between the CMV and the target. The CMV comprises ribonucleotides and deoxyribonucleotides and nucleotide analogs of each (generically "nucleobases"). The application discloses that CMV contain at least two segments of at least 3 ribo-type nucleobases paired to deoxyribo-type nucleobases, which regions flank the region of the CMV that corresponds to the mutation to be introduced into the target gene. The ribo-type nucleobases should preferably be nuclease resistant i.e., other than naturally occurring ribonucleotides. The uses of CMV include gene therapy of genetic diseases and construction of transgenic plants and animals.

32 Claims, 7 Drawing Sheets

```
        TGCGCG-ucgcggcggaTGCGGgugagccgacT
    T                                    T
    T         3'5'                       T        Ch1
        TCGCGC AGCGCCGCCTACGCCCACTCGGCTGT TGCGCG-ucgcggcggaTGTGGgugagccgacT
    T                                    T
    T         3'5'                       T        Ch2
        TCGCGC AGCGCCGCCTACACCCACTCGGCTGT TCGCGC-agcgccgccuACGCCcacucggcugT
    T                                    T
    T         5'3'                       T        Ch3
        TGCGCG TCGCGGCGGATGCGGGTGAGCCGACT TGCGCG-TCGCGGCGGATGCGGGTGAGCCGACT
    T                                   T
    T         3'5'                      T         Dh1
    T TCGCGC AGCGCCGCCTACGCCCACTCGGCTGT T
```

FIG. 2A

```
                    *
    →   T
        AC CTG ACT CCT GTG GAG AAG TCT GC              βS
        TG GAC TGA GGA CAC CTC TTC AGA CG
                    *
        AC CTG ACT CCT GAG GAG AAG TCT GC              βA
        TG GAC TGA GGA CTC CTC TTC AGA CG
                    *
        AT CTG ACT CCT GAG GAG AAG ACT GC              δ
        TA GAC TGA GGA CTC CTC TTC TGA CG

T GCGCG ug gac uga ggA CTC Cuc uuc aga cg T T       SC1
  T T CGCGC AC CTG ACT CCT GAG GAG AAG TCT GC T T      βS→βA
        3' 5'
                    *
   T GCGCG ug gac uga ggA CAC Cuc uuc aga cg T T       SC2
  T T CGCGC AC CTG ACT CCT GTG GAG AAG TCT GC T T      βA→βS
        3' 5'
                    *
   T GCGCG ua gac uga ggA CTC Cuc uuc uga cg T T       SC3
  T T CGCGC AT CTG ACT CCT GAG GAG AAG ACT GC T T      3 MISMATCHES TO
        3' 5'                                          βS
                    *
   T GCGCG ug gac uga ggA CTC Cuc uuc uga cg T T       SC4
  T T CGCGC AC CTG ACT CCT GAG GAG AAG ACT GC T T      2 MISMATCHES TO
        3' 5'                                          βS
                    *
  T T CGCGC ac cug acu ccT GTG Gag aag ucu gc T T      SC5
  T T GCGCG TG GAC TGA GGA CAC CTC TTC AGA CG T T      TARGETS THE NON-
        5' 3'                                          TEMPLATE STRAND OF
                                                       βA
```

FIG.3

SEQUENCE LISTING ( 1 ) GENERAL INFORMATION:

( i i i ) NUMBER OF SEQUENCES: 25

( 2 ) INFORMATION FOR SEQ ID NO:1:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:1:

CCGCCTACAC CCACTCG											17

( 2 ) INFORMATION FOR SEQ ID NO:2:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:2:

CCGCCTACGC CCACTCG											17

( 2 ) INFORMATION FOR SEQ ID NO:3:

( i ) SEQUENCE CHARACTERISTICS:
      ( A ) LENGTH: 21 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:3:

CAATGTCCCT GATGTTATGC A										21

( 2 ) INFORMATION FOR SEQ ID NO:4:

( i ) SEQUENCE CHARACTERISTICS:
      ( A ) LENGTH: 18 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:4:

CGCTGGGCCA AGGACGCT											18

( 2 ) INFORMATION FOR SEQ ID NO:5:

( i ) SEQUENCE CHARACTERISTICS:
      ( A ) LENGTH: 21 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:5:

CAATGTCCCT GATGTTATGC A										21

( 2 ) INFORMATION FOR SEQ ID NO:6:

( i ) SEQUENCE CHARACTERISTICS:
      ( A ) LENGTH: 18 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:6:

CGCTGGGCCA AGGACGCT											18

( 2 ) INFORMATION FOR SEQ ID NO:7:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:7:

TCCTAAGCCA GTGCCAGAAG A     21

( 2 ) INFORMATION FOR SEQ ID NO:8:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:8:

CTATTGGTCT CCTTAAACCT G     21

( 2 ) INFORMATION FOR SEQ ID NO:9:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:9:

CTCACAAACT AATGAAACCC TGC     23

( 2 ) INFORMATION FOR SEQ ID NO:10:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:10:

GAAAACAGCC CAAGGGACAG     20

( 2 ) INFORMATION FOR SEQ ID NO:11:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:11:

TCCTAAGCCA GTGCCAGAAG A     21

( 2 ) INFORMATION FOR SEQ ID NO:12:

( i ) SEQUENCE CHARACTERISTICS:

(A) LENGTH: 21 base pairs
                    (B) TYPE: nucleic acid
                    (C) STRANDEDNESS: single
                    (D) TOPOLOGY: linear (ii) MOLECULE TYPE: DNA (xi) SEQUENCE DESCRIPTION: SEQ ID NO:12:

CTATTGGTCT CCTTAAACCT G                                                                    21

(2) INFORMATION FOR SEQ ID NO:13:

(i) SEQUENCE CHARACTERISTICS:
                    (A) LENGTH: 24 base pairs
                    (B) TYPE: nucleic acid
                    (C) STRANDEDNESS: single
                    (D) TOPOLOGY: linear (ii) MOLECULE TYPE: DNA (xi) SEQUENCE DESCRIPTION: SEQ ID NO:13:

CTCACAAACC TAATGAAACC CTGC                                                                 24

(2) INFORMATION FOR SEQ ID NO:14:

(i) SEQUENCE CHARACTERISTICS:
                    (A) LENGTH: 20 base pairs
                    (B) TYPE: nucleic acid
                    (C) STRANDEDNESS: single
                    (D) TOPOLOGY: linear (ii) MOLECULE TYPE: DNA (xi) SEQUENCE DESCRIPTION: SEQ ID NO:14:

GAAAACAGCC CAAGGGACAG                                                                      20

(2) INFORMATION FOR SEQ ID NO:15:

(i) SEQUENCE CHARACTERISTICS:
                    (A) LENGTH: 68 base pairs
                    (B) TYPE: nucleic acid
                    (C) STRANDEDNESS: single
                    (D) TOPOLOGY: linear (ii) MOLECULE TYPE: DNA (ix) FEATURE:
                    (A) NAME/KEY: Cb1
                    (B) LOCATION: 1...68
                    (D) OTHER INFORMATION:

(xi) SEQUENCE DESCRIPTION: SEQ ID NO:15:

AGCGCCGCCT ACGCCCACTC GGCTGTTTTC AGCAGCGUGG GCGTAGGCGG CGCUGCGCGT                           60

TTTCGCGC                                                                                   68

(2) INFORMATION FOR SEQ ID NO:16:

(i) SEQUENCE CHARACTERISTICS:
                    (A) LENGTH: 68 base pairs
                    (B) TYPE: nucleic acid
                    (C) STRANDEDNESS: single
                    (D) TOPOLOGY: linear (ii) MOLECULE TYPE: DNA (ix) FEATURE:
                    (A) NAME/KEY: Cb2
                    (B) LOCATION: 1...68
                    (D) OTHER INFORMATION:

(xi) SEQUENCE DESCRIPTION: SEQ ID NO:16:

AGCGCCGCCT ACACCCACTC GGCTGTTTTC AGCCGAGUGG GTGTAGGCGG CGCUGCGCGT    60

TTTCGCGC    68

( 2 ) INFORMATION FOR SEQ ID NO:17:

( i ) SEQUENCE CHARACTERISTICS:
        ( A ) LENGTH: 68 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: Ch3
        ( B ) LOCATION: 1...68
        ( D ) OTHER INFORMATION:

( x i ) SEQUENCE DESCRIPTION: SEQ ID NO:17:

GCGCGTTTTC GCGCAGCGCC GCCUACGCCC ACUCGGCUGT TTTCAGCCGA GTGGGCGTAG    60

GCGGCGCT    68

( 2 ) INFORMATION FOR SEQ ID NO:18:

( i ) SEQUENCE CHARACTERISTICS:
        ( A ) LENGTH: 68 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: Dh1
        ( B ) LOCATION: 1...68
        ( D ) OTHER INFORMATION:

( x i ) SEQUENCE DESCRIPTION: SEQ ID NO:18:

AGCGCCGCCT ACGCCCACTC GGCTGTTTTC AGCCGAGTGG GCGTAGGCGG CGCTGCGCGT    60

TTTCGCGC    68

( 2 ) INFORMATION FOR SEQ ID NO:19:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:19:

ACCCCCAGCG CCGCCTACAC CCACTCGGCT GACCGG    36

( 2 ) INFORMATION FOR SEQ ID NO:20:

( i ) SEQUENCE CHARACTERISTICS:
        ( A ) LENGTH: 68 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: SC1
        ( B ) LOCATION: 1...68
        ( D ) OTHER INFORMATION:

( x i ) SEQUENCE DESCRIPTION: SEQ ID NO:20:

ACCTGACTCC TGAGGAGAAG TCTGCTTTTG CAGACUUCUC CTCAGGAGUC AGGUGCGCGT    60

TTTCGCGC    68

( 2 ) INFORMATION FOR SEQ ID NO:21:

( i ) SEQUENCE CHARACTERISTICS:
      ( A ) LENGTH: 68 base pairs
      ( B ) TYPE: nucleic acid
      ( C ) STRANDEDNESS: single
      ( D ) TOPOLOGY: linear ( i i ) MOLECULE TYPE: DNA ( i x ) FEATURE:
      ( A ) NAME/KEY: SC2
      ( B ) LOCATION: 1...68
      ( D ) OTHER INFORMATION:

( x i ) SEQUENCE DESCRIPTION: SEQ ID NO:21:

ACCTGACTCC TGTGGAGAAG TCTGCTTTTG CAGACUUCUC CACAGGAGUC AGGUGCGCGT    60

TTTCGCGC    68

( 2 ) INFORMATION FOR SEQ ID NO:22:

( i ) SEQUENCE CHARACTERISTICS:
      ( A ) LENGTH: 68 base pairs
      ( B ) TYPE: nucleic acid
      ( C ) STRANDEDNESS: single
      ( D ) TOPOLOGY: linear ( i i ) MOLECULE TYPE: DNA ( i x ) FEATURE:
      ( A ) NAME/KEY: SC3
      ( B ) LOCATION: 1...68
      ( D ) OTHER INFORMATION:

( x i ) SEQUENCE DESCRIPTION: SEQ ID NO:22:

ATCTGACTCC TGAGGAGAAG ACTGCTTTTG CAGUCUUCUC CTCAGGAGUC AGAUGCGCGT    60

TTTCGCGC    68

( 2 ) INFORMATION FOR SEQ ID NO:23:

( i ) SEQUENCE CHARACTERISTICS:
      ( A ) LENGTH: 68 base pairs
      ( B ) TYPE: nucleic acid
      ( C ) STRANDEDNESS: single
      ( D ) TOPOLOGY: linear ( i i ) MOLECULE TYPE: DNA ( i x ) FEATURE:
      ( A ) NAME/KEY: SC4
      ( B ) LOCATION: 1...68
      ( D ) OTHER INFORMATION:

( x i ) SEQUENCE DESCRIPTION: SEQ ID NO:23:

ACCTGACTCC TGAGGAGAAG ACTGCTTTTG CAGUCUUCUC CTCAGGAGUC AGGUGCGCGT    60

TTTCGCGC    68

( 2 ) INFORMATION FOR SEQ ID NO:24:

( i ) SEQUENCE CHARACTERISTICS:
      ( A ) LENGTH: 68 base pairs
      ( B ) TYPE: nucleic acid
      ( C ) STRANDEDNESS: single
      ( D ) TOPOLOGY: linear

```
        ( i i ) MOLECULE TYPE: DNA ( i x ) FEATURE:
                ( A ) NAME/KEY: SC5
                ( B ) LOCATION: 1...68
                ( D ) OTHER INFORMATION:

( x i ) SEQUENCE DESCRIPTION: SEQ ID NO:24:

GCGCGTTTTC   GCGCACCUGA   CUCCTGTGGA   GAAGUCUGCT   TTTGCAGACT   TCTCCACAGG        60

AGTCAGGT                                                                           68

( 2 ) INFORMATION FOR SEQ ID NO:25:

( i ) SEQUENCE CHARACTERISTICS:
                ( A ) LENGTH: 25 base pairs
                ( B ) TYPE: nucleic acid
                ( C ) STRANDEDNESS: single
                ( D ) TOPOLOGY: linear ( i i ) MOLECULE TYPE: DNA ( i x ) FEATURE:
                ( A ) NAME/KEY: Delta
                ( B ) LOCATION: 1...25
                ( D ) OTHER INFORMATION:

( x i ) SEQUENCE DESCRIPTION: SEQ ID NO:25:

ATCTGACTCC   TGAGGAGAAG   ACTGC                                                    25
```

CHIMERIC MUTATIONAL VECTORS HAVING NON-NATURAL NUCLEOTIDES

FIELD OF THE INVENTION

The invention concerns compounds and methods of their use to make specific genetic alterations in the genome of target eukaryotic cells. More specifically, the invention concerns the introduction into the nucleus of the target cell of an oligonucleobase compound, termed a Chimeric Mutational Vector (CMV), having a sequence that has regions of homology and one or more differences with a gene of the target cell that is to be altered (the "target gene"). The structure of the CMV is designed so that genetic recombination between the CMV and the target gene occurs, i.e., the sequence of the CMV replaces the sequence of the target gene.

BACKGROUND OF THE INVENTION

Site-Directed Genetic Alteration in Eukaryotic Cells

Those skilled in the art of molecular biology recognize that on frequent occasions it is desired not merely to introduce a new polynucleic acid sequence, i.e., a new gene, into a targeted eukaryotic cell, but rather to alter a defined, pre-existing gene in the targeted cell. The targeted cell can be used in culture or it can be used to construct a transgenic animal.

A wide variety of techniques have been developed to introduce DNA into cultured eukaryotic cells. These techniques include calcium phosphate precipitation and DEAE-dextran mediated endocytosis, electroporation, liposome mediated fusion and transduction with replication incompetent viruses. However, while such techniques can quite often introduce functional genes into the eukaryotic cell, these techniques do not readily accomplish an alteration (mutation) in a specific existing gene. After introduction the exogenous DNA is isolated at a random position in the cell's genome by illegitimate recombination, rather than at a specific position by homologous recombination.

Prior to the present invention, there was no generally satisfactory scheme for introducing a site-specific genetic alteration in a higher eukaryote, i.e., in mammalian or avian cells. Although homologous recombination can be obtained in higher eukaryotic cells by introduction of very long (>1 kb) nucleic acids, these techniques require the application of elaborate selection techniques because the rate of illegitimate recombination in higher eukaryotes greatly exceeds that of homologous recombination. Thomas, K. R. & Capecchi, M. R., 1987, Cell 52: 503. See, also, Valancius, V. & Smithies O., 1991, Mol. Cell. Biol. 11: 4389 (comparison homologous recombination of linearized and supercoiled plasmids in eukaryotic cells).

One approach to achieving a predominantly site-directed mutagenesis has been the introduction of single stranded oligodeoxynucleotides directly into the cell. This techniques has been successfully employed in the yeast *Saccharomyces cerevisiae*, in which homologous recombination is significantly more active than it is in higher eukaryotes. Moerschell, R. P., et al., 1988, Proc. Natl. Acad. Sci. 85: 524–28; Yamamoto, T., et al., 1992, Yeast 8: 935–48. However, to date there have been no reports of the successful transformation of mammalian or avian cells by single stranded oligonucleotides.

A relationship between the structure of the target DNA and the rate of homologous recombination in mammalian can be inferred by studies that show that regions of alternating purine and pyrimidine bases, i.e., $[d(TG)_{30} \cdot d(AC)_{30}]$, display an entranced rate of recombination. These effects were demonstrated in studies of non-replicating plasmids in cultured mammalian cells. Wahls, W. P., et al., 1990, Mol. Cell. Biol. 10: 785–93. These experiments were not extended to show recombination between an exogenous nucleic acid and the genome of the cell.

Attempts have been made to use RecA, a protein that promotes homologous recombination in the bacteria, *E. coli*, to promote homologous recombination in eukaryotic cells. However, these attempts have not been clearly successful. For example U.S. Pat. No. 4,950,599 to W. Bertling discloses a very low rate of site-directed mutation and no enhancement in the rate of homologous recombination by use of RecA in eukaryotic cells. Patent publications WO 93/22443 to D. Zarling and E. Sena, and publication 94/04032 to D. C. Gruenert and K. Kunzelmann both purport to correct a genetic defect in a cultured cell line related to cystic fibrosis. These publications disclose primarily experimental data that demonstrate the principle rather than data concerning examples of operative methods. Thus, to introduce polynucleotide/RecA complexes access to the nucleus, Zarling and Gruenert employ cells that were membrane-permeabilized, although such cells are incapable of further growth. Moreover, even when RecA-promoted homologous recombination was asserted to have taken place in intact cells, these publications provide no quantitative estimates of its frequency. Thus, the use of prokaryotic recA has not been convincingly shown to result in a rate homologous recombination in any viable eukaryotic cell significantly greater than the spontaneous rate of homologous recombination.

Chimeric Oligonucleotides having DNA•RNA Base Pairs

The inclusion of a publication or patent application in this section is not to be understood as an admission that the publication or application occurred prior to the present invention or resulted from the conception of a person other than the inventor.

An oligonucleotide having complementary deoxyribonucleotides and ribonucleotides and containing a sequence homologous to a fragment of the bacteriophage M13mp19, was described in Kmiec, E. B., et al., November 1994, Mol. and Cell. Biol. 14: 7163–7172. The oligonucleotide had a single contiguous segment of ribonucleotides. Kmiec et al. showed that the oligonucleotide was a substrate for the REC2 homologous pairing enzyme from *Ustilago maydis*.

Patent publication WO 95/15972, published Jun. 15, 1995, and corresponding U.S. patent application Ser. No. 08/353,657, filed Dec. 9, 1994, by E. B. Kmiec, described CMV for the introduction of genetic changes in eukaryotic cells. Examples in a *Ustilago maydis* gene and in the murine ras gene were reported. The latter example was designed to introduce a transforming mutation into the ras gene so that the successful mutation of the ras gene in NIH 3T3 cells would cause the growth of a colony of cells ("transformation"). The WO 95/15972 publication reported that the maximum rate of transformation of NIH 3T3 was less than 0.1%, i.e., about 100 transformants per $10^6$ cells exposed to the ras CMV. In the *Ustilago maydis* system the rate of transformants was about 600 per $10^6$. A chimeric vector designed to introduce a mutation into a human bcl-2 gene was described in Kmiec, E. B., February 1996, Seminars in Oncology 23: 188.

A CMV designed to repair the mutation in codon 12 of K-ras was described in Kmiec, E. B., December 1995, Advanced Drug Delivery Reviews 17: 333–40. The CMV was tested in Capan 2, a cell line derived from a human pancreatic adenocarcinoma, using LIPOFECTIN™ to introduce the CMV into a the Capan 2 cells. Twenty four hours after exposure to the CMV, the cells were harvested and genomic DNA was extracted; a fragment containing codon 12 of K-ras was amplified by PCR and the rate of conversion estimated by hybridization with allele specific probes. The rate of repair was reported to be approximately 18%.

A CMV designed to repair a mutation in the gene encoding liver/bone/kidney type alkaline phosphatase was reported in Yoon, K., et al., March 1996, Proc. Natl. Acad. Sci. 93: 2071. The alkaline phosphatase gene was transiently introduced into CHO cells by a plasmid. Six hours later the CMV was introduced. The plasmid was recovered at 24 hours after introduction of the CMV and analyzed. The results showed that approximately 30 to 38% of the alkaline phosphatase genes were repaired by the CMV.

U.S. patent application Ser. No. 08/640,517, filed May 1, 1996, by E. B. Kmiec, A. Cole-Strauss and K. Yoon, discloses methods and CMV that are useful in the treatment of genetic diseases of hematopoietic cells, e.g., Sickle Cell Disease, Thalassemia and Gaucher Disease.

BRIEF DESCRIPTION OF THE FIGURES

FIGS. 2A and 2B. FIG. 2A shows the sequence and structure of oligonucleotide Dh1 (SEQ ID NO: 18) and chimeric oligonucleotides Ch1, Ch2 and Ch3. (SEQ ID NO: 15), (SEQ ID NO: 16), and (SEQ ID NO: 17) FIG. 2B illustrates the relationship between the sequence of CMV Ch1 and the alkaline phosphatase gene (SEQ ID NO: 19). DNA nucleotides are UPPER CASE; RNA nucleotides are lower case.

FIG. 3. The sequences of the codons 3–9 and adjacent dinucleotides of codons 2 and 10 of $\beta^S$-globin (nt 1–25 of SEQ ID NO: 21), $\beta^A$-globin (nt 1–25 of SEQ ID NO: 20), δ-globin (SEQ ID NO: 25), and chimeric vectors SC1–SC5 (SEQ ID NO: 20–24, respectively) DNA and RNA nucleotides are indicated as in FIG. 2A.

FIG. 4A and 4B show the fraction of copies of β-globin converted from $\beta^S$ to $\beta^A$ as a function of nM SC1 added and of $\beta^A$ to $\beta^S$ as a function nM of SC2, respectively, in cultures of EB-transformed lymphoblasts.

FIG. 5 shows the fraction of copies of β-globin converted $\beta^A$ to $\beta^S$ as a function of ng SC2 added to cultures of cd34$^+$ hematopoietic stem cells.

DEFINITIONS

Figure 1:
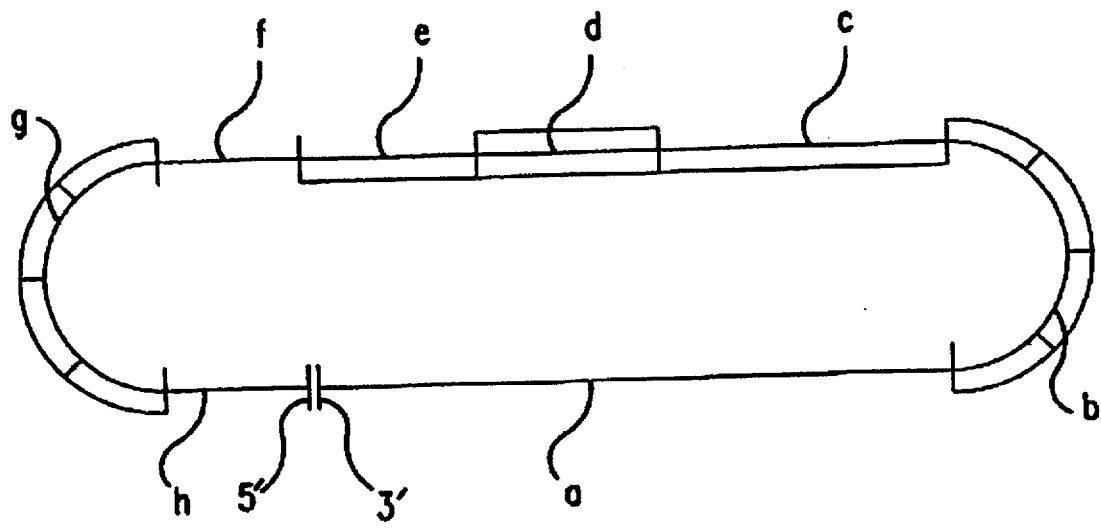
FIG. 1. General form of one embodiment of a Chimeric Mutational Vector.

The invention is to be understood in accordance with the following definitions.

An oligonucleobase is a polymer of nucleobases that can hybridize by Watson-Crick base pairing to a DNA having the complementary sequence.

Nucleobases comprise a base, which is a purine, pyrimidine, or a derivative or analog thereof.

Nucleobases include peptide nucleobases, the subunits of peptide nucleic acids, and morpholine nucleobases as well as nucleosides, nucleotoids and nucleotides. Nucleosides are nucleobases that contain a pentosefuranosyl moiety, e.g., an optionally substituted riboside or 2'-deoxyriboside, and have a linkage to other nucleobases that does not contain a phosphorus. Nucleotoids are pentosefuranosyl containing nucleobases having linkages that contain phosphorus, e.g., phosphorothioates, phosphoramidates and methylphosphonates, but not phosphates. Nucleotides are pentosefuranosyl containing nucleobases that are linked by phosphodiesters.

A oligonucleobase chain has a single 5' and 3' terminus, which are the ultimate nucleobases of the polymer. A particular oligonucleobase chain can contain nucleobases of all types. An oligonucleobase compound is a compound comprising one or more oligonucleobase chains that are complementary and hybridized by Watson-Crick base pairing.

Nucleobases are either deoxyribo-type or ribo-type. Ribo-type nucleobases are pentosefuranosyl containing nucleobases wherein the 2' carbon is a methylene substituted with a hydroxyl, alkyloxy or halogen. Deoxyribo-type nucleobases are nucleobases other than ribo-type nucleobases and include all nucleobases that do not contain a pentosefuranosyl moiety.

An oligonucleobase strand generically includes both oligonucleobase chains and segments or regions of oligonucleobase chains. An oligonucleobase strand has a 3' end and a 5' end. When a oligonucleobase strand is coextensive with a chain, the 3' and 5' ends of the strand are also 3' and 5' termini of the chain.

A region is a portion of an oligonucleobase, the sequence of which is derived from some particular source, e.g., a CMV having a region of at least 15 nucleotides having the sequence of a fragment of the human β-globin gene. A segment is a portion of a CMV having some characteristic structural feature. A given segment or a given region can contain both 2'-deoxynucleotides and ribonucleotides. However, a ribo-type segment or a 2'-deoxyribo-type segment contain only ribo-type and 2'-deoxyribo-type nucleobases respectively.

SUMMARY

The present invention provides oligonucleobase compounds, termed Chimeric Mutational Vectors (CMV). CMV can be used to introduce specific genetic changes in plant and animal cells. The invention is applicable to in the field of medicine for gene therapy, and in the fields of biomedical research, pharmaceutical production and agriculture to construct specifically mutated plants and animals. A CMV comprises two complementary oligonucleobase strands. The two strands can be present on a single chain or on two chains that can be optionally linked by any chemistry for cross-linking oligonucleotides.

The sequence of the strands of a CMV is homologous to the target gene except for a mutator region which introduces the genetic change into the target gene. The CMV can also contain regions having a sequence unrelated to the target gene. The mutator region must be directly adjacent in both 3' and 5' directions to a homology region of at least one base.

The oligonucleobases of the CMV are either ribo-type or 2'-deoxyribo-type. Ribo-type nucleobases contain a pentosefuranosyl moiety having a 2' oxygen or halogen. At least three contiguous bases of the homologous region of the first strand are ribo-type nucleobases that are Watson-Crick base paired to deoxyribo-type nucleobases of the second strand. Nucleobases that are sensitive to RNase are not preferred for use in the invention.

DETAILED DESCRIPTION OF THE INVENTION

The present invention provides compounds, termed Chimeric Mutational Vectors (CMV) that can be used to make specific changes in the genome of a eukaryotic cell. The CMV are comprised of polymers of purines and pyrimidines that hybridize, i.e., form a Watson-Crick base pairs of purines and pyrimidines, to DNA having the appropriate sequence. Each CMV is divided into a first and a second strand of at least 15 bases each that are complementary to each other and can be, but need not be, covalently linked. The polymers of purines and pyrimidines, termed oligonucleobases, are comprised of two types of subunits, termed nucleobases. There are two types of nucleobases. Ribo-type nucleobases are ribonucleosides having a 2'hydroxyl, substituted hydroxyl or 2'halo-substituted ribose. All nucleobases other than ribo-type nucleobases are deoxyribo-type nucleobases.

The sequence of the first and second strands consists of at least two regions that are homologous to the target gene and one or more regions (the "mutator regions") that differ from the target gene and introduce the genetic change into the target gene. The mutator region is directly adjacent to homologous regions in both the 3' and 5' directions. In a preferred embodiment of the invention, each mutator region is adjacent in both the 3' and 5' directions to homologous regions of at least three bases. In a preferred embodiment of the invention, each mutator region is flanked in both the 3' and 5' directions by ribo-type oligonucleobase segments of at least three bases, which segments need not be adjacent to the mutator region. The flanking ribo-type nucleobase segments need not be directly adjacent to the mutator region, i.e., a portion of the homologous region comprising deoxyribo-type nucleobases can intervene. The total length of all homologous regions is preferably at least 14 bases. If the CMV contains two homologous regions separated by a mutator region, the homologous regions can more preferably be each between 8 and 12 bases long and most preferably be 10 bases long.

At least two homologous regions of the first strand are comprised of at least three contiguous ribo-type nucleobases which are Watson-Crick paired to deoxyribo-type nucleobases of the second strand. In a preferred embodiment there are between 9 and 25 ribo-type nucleobases and more preferably 20 ribo-type nucleobases in the first strand, which are Watson-Crick paired to deoxyribo-type nucleobases of the second strand. In one embodiment there are no ribo-type nucleobases in the second strand. In one embodiment the mutator region of the first strand consists of deoxyribo-type nucleobases and is flanked by deoxyribo-type nucleobases. Alternatively, the mutator region can be comprised of ribo-type nucleobases of the first strand and deoxyribo-type nucleobases of the second strand.

The CMV is still further characterized by containing at least three nuclease resistant ribo-type nucleobases. In a preferred embodiment all ribo-type nucleobases are nuclease resistant.

The mutator region can be as large as 2 kilobases and can encode an exon. Preferably the mutator region consists of 20 or fewer bases, more preferably 6 or fewer bases and most preferably 3 or fewer bases. The mutator region can be of a length different than the length of the sequence that separates the regions of the target gene homologous with the homologous regions of the CMV so that an insertion or deletion of the target gene results. When the CMV is used to introduce a deletion there is no base identifiable as within the mutator region. Rather, the mutation is effected by the juxtaposition of the two homologous regions that are separated in the target gene. In one embodiment the mutator region is a deletion of from 6 to 1 bases or more preferably from 3 to 1 bases. Multiple separated mutations can be introduced by a single CMV, in which case there are multiple mutator regions in the same CMV. Alternatively multiple CMV can be use simultaneously to introduce multiple genetic changes in a single gene or, alternatively to introduce genetic changes in multiple genes of the same cell.

In a preferred embodiment the CMV is resistant to RNase. Therefore, the use of only naturally occurring ribo-type nucleobases, which are sensitive to RNase, is not suitable for use in the invention. The ribo-type nucleobases of a CMV should include at least three ribo-type nucleobases preferably selected from non-phosphodiester linked ribonucleotides ("ribonucleotoids"), 2'O-substituted or 2'haloribonucleotides, 2'O-substituted or 2'haloribonucleotoids, and ribonucleosides, which can be optionally 2' substituted. In a preferred embodiment of the CMV, no nuclease sensitive, i.e., 2'O-ribonucleotides, are used.

In one embodiment the CMV is a single oligonucleobase chain of between 40 and 100 bases. In an alternative embodiment, the CMV comprises a first and a second oligonucleobase chain, each of between 20 and 100 bases; wherein the first chain comprises the first strand and the second chain comprises the second strand. The first and second chains can be linked covalently or, alternatively, can be associated only by Watson-Crick base pairings.

6.1 Uses of Chimeric Mutational Vectors

Chimeric Mutational Vectors can be used to introduce changes into the sequence any eukaryotic gene, which has a known sequence. The change can result in the replacement of one or more nucleotides or can be an insertion or deletion of one or more nucleotides. In preferred embodiments the replacement, insertion or deletion can be of 20 or fewer contiguous bases, in a more preferred embodiment the replacement, insertion or deletion can be of 6 or fewer bases and most preferably of 3 or fewer bases. The insertion can be as long as about two kilobases. The insertions or deletions can be made in the coding and the regulatory parts of the gene.

Cells can be transfected with the CMV by any technique now known or to be developed for transfecting cells with DNA. Such techniques include electroporation, liposome transfer and calcium phosphate precipitation. In one embodiment the transfection is performed with a liposomal transfer compound, e.g., DOTAP (N-[1-(2,3-Dioleoyloxy) propyl]-N,N,N-trimethylammonium methylsulfate, Boehringer-Mannheim) or an equivalent, such as LIPOFECTIN. The amount of CMV is not critical to the practice of the invention; good results can be achieved with 10 mM/$10^5$ cells. A ratio of about 500 ng of CMV in 3 µg of DOTAP per $10^5$ cells can be used. The transfection technique of Examples 1–3, infra., can be used with the modification that the transfected cells are cultured in serum free media, media supplemented with human serum albumin or human serum.

The present invention encompasses methods of using Chimeric Mutational Vectors. Uses of Chimeric Mutational Vectors include the repair of genetic diseases such as Gaucher Disease, thalassemia and Sickle Cell disease. Other applications include the introduction of stop codons or frame shift mutations to make "knock-outs," i.e., transgenic animals or plants that lack a functional copy of a specific gene, as well as transgenic animals or plants having specific mutations. In a still further method of use encompassed by the invention specific mutations can be made for the purpose of studying the structure function relationships of genes-of-interest. Alternatively, if a desirable mutation has been identified in one species, it can be introduced in the homologous genes of other species by use of the CMV.

For medical purposes, the invention can be used to repair mutations or introduce mutations into any cell-type that can be removed from a subject's body, cultured and reimplanted into the subject. Techniques for the removal, culture and reimplantation of hepatocytes, in particular of hepatic reserve (stem) cells, have been described in patent publication W094/08598 to Naughton, G. B. and Sibanda, B., Apr. 28, 1994. Examples of genetic diseases that can be cured by repair of mutations in hepatocytes include: familial hypercholesteremia, caused by mutation in the LDL receptor; emphysema that caused by a mutation in the α1-antitrypsin gene; and hemophilia and Christmas Disease, which are caused by mutations in coagulation factors VIII and IX, respectively.

In a yet further use of the invention, CMV can be used to mutagenize a population of cells so that a mutant, having a selectable phenotype can be obtained. According to this aspect of the invention, a mixture of CMV having a mutator region of one or several nucleotides is synthesized so that the three non-wild type nucleotides are present at each position of the mutator region. The treatment of a population of cells with such a mixture of CMV will induce a variety of mutations in the target gene. After an appropriate selection step, a mutant having the desired phenotype can be recovered.

6.2 Structure of Exemplary Chimeric Mutational Vectors

6.2.1 Single Chain Chimeric Mutational Vectors

In one embodiment a Chimeric Mutational Vector (CMV) is a single 5',3'-linked oligonucleobase chain comprised of between about 40 and about 100 pentosefuranosyl containing nucleobases. A single chain CMV can contain unpaired nucleotides, which form one or two hair-pin turns, which turn or turns divide(s) the CMV into the first and second strands, so that at least 15 bases of the first strand can be Watson-Crick paired to bases of the second strand.

FIG. 1 shows the structure of one embodiment of a single-chain CMV with segments (a)–(h). In the embodiment of FIG. 1, the first strand consists of segments (c), (d) and (e), which is complementary to a second strand consisting of segment (a). In this particular embodiment the 3' terminus of the CMV is illustrated to be at the 3' end of the (a) segment and the 5' terminus is shown to be at the 5' end of the (h) segment. However, the location of the termini and the orientation of 3' and 5' directions of the CMV with respect to the segments can be elsewhere, so long as the termini do not interrupt the homologous or mutator regions of the first or second strands. The segments are labeled sequentially (a) through (h).

In one embodiment the lengths and characteristics of the segments are as follows. Segment (a) is between 16 and 40 nucleotides and preferably between 20 and 30 nucleotides. The sequence of the region of segment (a) can be either that of the coding strand or the non-coding strand of the gene that contains the intended mutation (the "mutated target gene"). The location of the sequence of segment (a) must include the portion of the target gene that is to be changed. Unless the target gene is not normally transcribed in target cell, it is preferred that the sequence of segment (a) is the sequence of the coding strand of the target gene. When the target gene is not transcribed in the target cell, then neither the coding strand sequence or the non-coding strand sequence is preferred. The sequence of segment (a) determines the sequences and combined lengths of segments (c)–(e), which must be complementary to segment (a).

The oligonucleobases of the portion of segment (a) that are base paired with segments (c) and (e) can be any 2'-deoxyribo-type nucleobases The nucleobase of segments (c) and (e), which are termed ribonucleotide segments, can be any ribo-type nucleobase 2' O-ribonucleotides, i.e., nucleotides that is known or will be developed. In a preferred embodiment, the nucleotides of segment (d), which is termed the intervening segment are 2'-deoxyribo-type nucleobases. Alternatively, segment (d) can be made of ribo-type nucleobases; in which case the boundaries between segments (c), (d) and (e) are not defined. Segments (b) and (f) through (h) can be of any type of nucleobase.

In a preferred embodiment, the sequence of segments (c) and (e) are completely homologous to the target gene. However, a one base mutator region in the (c) or (e) segment can result in the mutation of the target gene at the homologous position.

Segments (b) and (g) are about 4 nucleotides in length and form single stranded hairpin turns that allow segments (a) and (c)–(e) and segments (f) and (h) to form Watson-Crick base pairs, i.e., to form duplex nucleic acids. In alternative embodiments the function of segments (b) and (c), which is to covalently link the first and second strands, can be served by non-oligonucleobase moieties.

Segments (c) and (e), also termed the first and second ribo-type segments, consist, in one embodiment, of 2'-O-methylribonucleotides. In a preferred embodiment, segments (c) and (e) are independently, between 6 and 13 nucleotides.

Segment (d), also termed the intervening segment, in one embodiment, is between 4 and 20 nucleotides in length. If the target gene contains two or more point mutations that are separated by fewer than 15 nucleotides, each can be repaired by the same CMV.

Segments (f) and (h) form a duplex that brings the 3' and 5' ends of the CMV, which is nicked between segments (a) and (h) into juxtaposition. The structure formed by segments (f), (g) and (h) is termed a hairpin cap. A hairpin cap contains a terminal end and a nonterminal end. The terminal end forms a terminus of the chain, which can be either a 5' or a 3' terminus. The function of a hairpin cap is to control the position of the 3' or 5' terminus. The non-terminal end of the hairpin cap can be ligated to an end of a strand, whereby the end of the complementary strand, which is the second terminus of the chain is juxtaposed to the terminal end of the hairpin cap, as shown in FIG. 1. The 3' and 5' termini can be, in one embodiment, dephosphorylated. In an alternative embodiment, the 3' and 5' termini can be covalently linked by a phosphodiester bond or equivalent, so that the CMV is a closed circular oligonucleotide. Segments (f) and (h) can be optionally deleted from a closed circular CMV. In a preferred embodiment the orientation of the oligonucleobase of the hairpin cap is the same as the orientation of the strand to which it is linked. If the orientation of the hairpin cap is anti-parallel to the orientation of the strand to which it is attached, the designation as 3' or 5' of the terminal end of the hairpin is determined by the structure of terminal end of the complementary.

In a preferred embodiment, the CMV is a single chain CMV containing one hairpin cap, oriented in parallel with the chain, having juxtaposed 3' and 5' ends. There are eight specific embodiments of this type, which are defined by the location of the ligation between the hairpin cap and the chain and by whether the sequence of the first strand is the sequence of the coding strand or the non-coding strand of the target gene. The eight species are given in Table I. FIG. 1 illustrates species 2 and 6 of Table I.

TABLE I

| Species | Location of ligation of Hairpin Cap and Chain | Sequence of First Strand |
|---|---|---|
| 1 | 3' First Strand | Coding |
| 2 | 5' First Strand | Coding |
| 3 | 3' Second Strand | Coding |
| 4 | 5' Second Strand | Coding |
| 5 | 3' First Strand | Non-coding |
| 6 | 5' First Strand | Non-coding |
| 7 | 3' Second Strand | Non-coding |
| 8 | 5' Second Strand | Non-coding |

6.2.2 Dual Chain Chimeric Mutational Vectors

Alternatively, the CMV can comprise two chains, each chain having a 3' and a 5' terminus, wherein a first chain comprises the first strand and a second chain comprises a second strand. The first and second chains can be cross-linked by a covalent linker or the first and second chains can be held in association only by Watson-Crick bases pairing. The lengths of the regions and segments of the first and second strands of a two chain CMV are constructed according to the foregoing guides regarding single chain CMV. In one embodiment, the first and second chains can further comprise complementary segments of between 3 and 10 bases that flank the first and second strands that increase the stability of the association between the first and second chains.

An alternative embodiment of the two chain CMV can comprise two oligonucleobase chains and two hairpin caps; the first strand is a part of the first chain and the second strand is a part of the second chain. The hairpin caps can both be ligated to the ends of one strand. In one specific configuration, termed a "cradle" configuration, a hairpin cap is ligated to each end of the second strand. In an "anti-cradle" configuration, the hairpin caps are ligated to the ends of the first strand. An alternative type of configuration, termed "head-to-tail," consists of a hairpin cap ligated to each of the strands. Because the strands of the CMV hybridize only in an antiparallel fashion, there are only two specific configurations of the head-to-tail type: the hairpin caps can both be ligated to either the 3' ends or the 5' ends of the strands.

6.3 The Synthesis of CMV and Selection of Nucleobases

CMV can be synthesized by any technique used to synthesize oligonucleotides or oligonucleotide analogs. For CMV having chains up to about 100 bases in length, the preferred technique is solid-phase synthesis. Alternatively, subsegments of CMV chains greater than about 50 bases in length can be synthesized by solid phase synthesis and ligated by liquid phases techniques, well known to those skilled in the art. Wosnick, M. A., 1987, Gene 60: 115–117. As those skilled in the art appreciate, complementary subsegments can be synthesized by solid-phase techniques so that when annealed, the ends of the subsegments are staggered. By causing adjacent subsegments to have complementary staggered ends, adjacent segments can be ligated by well known enzymatic processes. By this technique a chain of a CMV considerably larger than 100 bases can be synthesized.

The nucleobases of a chain of a CMV can be any nucleobase now known or to be developed that hybridizes by Watson-Crick base pairing to DNA. Suitable nucleobases include nucleotides and nucleotoids. The structure and synthesis of oligonucleobases having exemplary nucleotoids can be found as follows: Phosphorothioates, Eckstein, F., Ann. Rev. Biochem., 1985, 54, 367; Phosphoramidates, Froehler, B. C., et al., Nucleic Acid Research, 1988, 16, 4831; Methylphosphonates, Miller, P. S., et al., 1985, Biochimie, 1985, 67, 769. A method of producing oligonucleotoids having chiral-specific phosphorus-containing linkages is described in U.S. Pat. No. 5,212,295. Chirally-specific oligonucleotides having the appropriately selected isomer hybridize to DNA with improved stability.

Pentosefuranosyl containing nucleobases that are linked by non-phosphorus nucleobases that can be used as deoxyribo-type nucleobases, which are termed nucleosides. Nucleosides that form duplexes with DNA that are at least as stable as DNA/DNA duplexes are linked by the various linkage chemistries. The chemistries and methods for their use in oligonucleobases are described as follows: methylhydroxylamine linkages, Vasseur et al., J. Am. Chem. Soc. 1992, 114, 4006, U.S. Pat. Nos. 5,386,023 and 5,489,677; alkylene dioxy linkages, U.S. Pat. No. 5,223,618; and 3'-Thioformacetal, Jones et al., J. Org. Chem. 1993, 58, 2983.

Other nucleosides that can be used in CMV include: Carbamates, Stirchak et el., J. Org. Chem. 1987, 52, 4202; Sulfonate & Sulfonamide, Glemarec et al., Tetrahedron 1993, 49, 2287, Reynolds et al., J. Org. Chem. 1992, 57, 2983; Sulfone, Huang, Z., J. Org. Chem. 1991, 56, 3869; Sulfamate, Huie, E. M., et al., J. Org. Chem., 1992, 57, 4569; and Diisopropylsilyl & silyl, Cormier and Ogilvie, Nucleic Acids Res. 1988, 16, 4583, Ogilvie & Cormier, Tetrahedron Lett. 1985, 26, 4159.

Pentosefuranosyl containing nucleobases can be of either the ribo-type or 2'-deoxyribo-type. At least three ribo-type nucleobases for use in CMV must be nuclease resistant. Suitable nuclease resistant ribo-type nucleobases can be selected from the group of ribonuclease resistant nucleobases, consisting of 2'AX-nucleosides, 2'AX-nucleotoids, 2'AR-nucleotides, where A=O, F, Cl or Br and when A=A, then X=H or $C_{1-6}$ and R=$C_{1-6}$, or when A is a halogen, then X and R are omitted.

Nucleobases that lack a pentosefuranosyl moiety can be used as deoxyribo-type nucleobases. Suitable examples include replacement of the pentosefuranosyl phosphate moiety by a Morpholino carbamate, Wang & Weller, Tetrahedron Lett., 1991, 32, 7385 and peptide nucleic acids in which the pentosefuranosyl phosphate moiety is replaced by an aminoethylglycine. Peptide nucleic acids (PNA) are described in Egholm et al., J. Am. Chem. Soc., 1992, 114, 1895 and Huang, B. S. et al., J. Org. Chem., 1991, 56, 5006 and WO 92/20703 to Buchardt et al.; methods of making PBA/oligonucleotide chimeric polymers is described in WO 95/14706.

Those skilled in the art understand that PNA can hybridize to DNA in either orientation, i.e., either end of a PNA can be the 3' or 5' end. Peffer, N. J., et al., 1993, Proc. Natl. Acad. Sci. 90: 10648–52. When a peptide nucleobase is present in an oligonucleobase strand having pentosefuranosyl-containing nucleobases, the 3' and 5' ends of the strand are determined by the orientation of the pentosefuranosyl moieties or, if none are present in the chain having the peptide nucleobase, then the 3' and 5' ends of the strand are determined by the orientation of pentosefuranosyl nucleobases of the complementary strand. Note, that the first strand of a CMV must contain at least three pentosefuranosyl nucleobases.

EXAMPLES

Example 7.1. The Use of CMV to Repair Episomal Alkaline Phosphatase

An expression plasmid containing the wild-type human liver/bone/kidney alkaline phosphatase cDNA under the control of the SV40 early promoter was obtained and designated pHAP. An identical plasmid with the mutant version of the cDNA was obtained and designated p711. The design of CMV to interconvert the sequences of pHAP and p711 are diagrammed in FIG. 2A. The CMVCh1 was designed to repair the missense mutation at position 711. It has a G residue, the wild-type sequence, at the site corresponding to the mutation. Ch2 has a design identical to Ch1 except for an A instead of G at the site corresponding to position 711. Ch3 has the same sequence as Ch1 but the sequence of the ribonucleotide segments is that of the coding strand of the alkaline phosphate gene instead of the noncoding strand. The oligonucleotide Dh1 contained the same sequence as Ch1, but contained only 2'-deoxynucleotides.

Figure 2B:
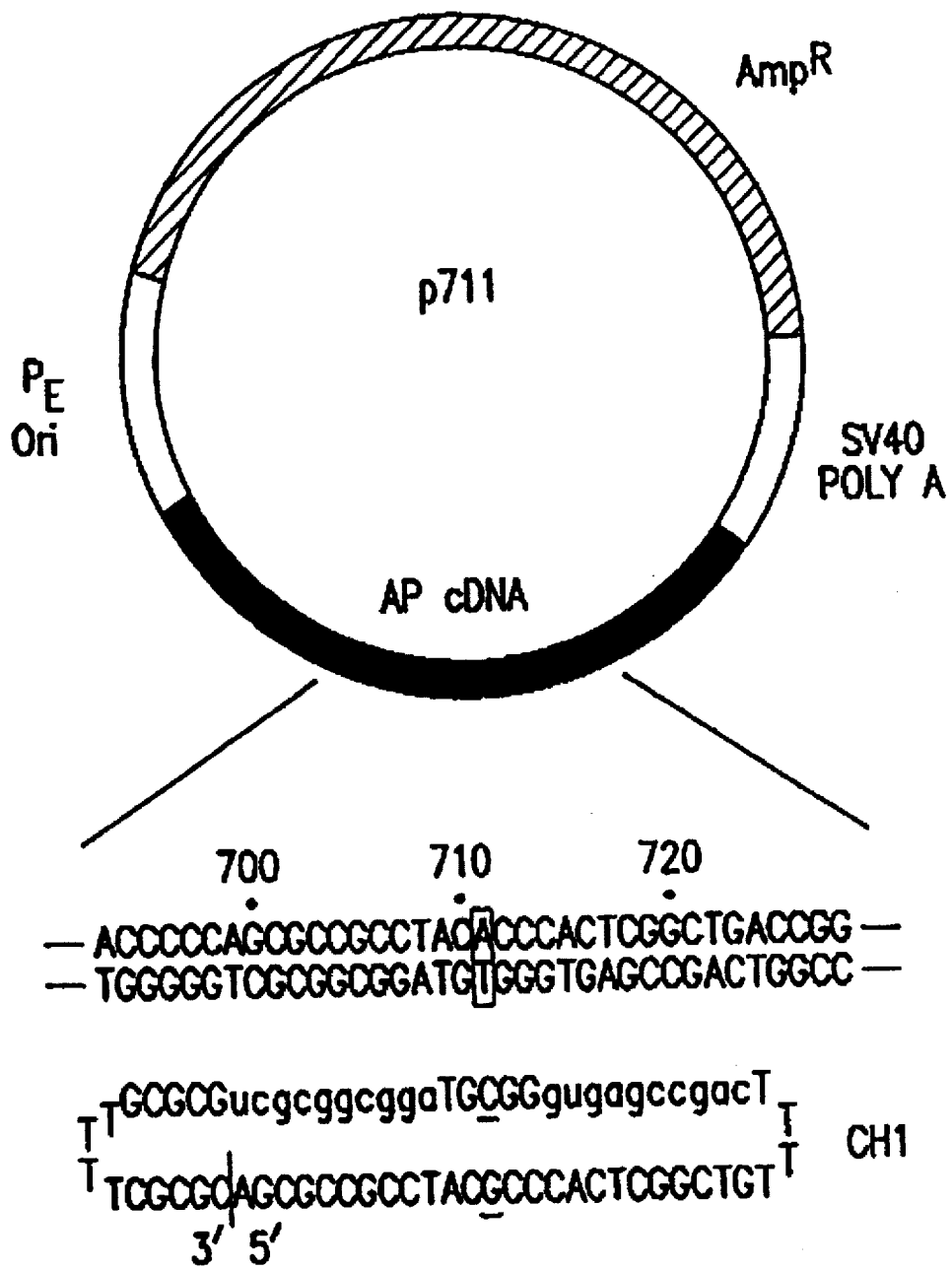

The schematic of p711 in FIG. 2B shows the single point mutation, A, at position 711 in the coding region of the alkaline phosphatase cDNA, the SV40 early promoter ($P_E$), SV40 origin of replication (ori), polyadenylation addition site and small-t intron sequence for splicing (SV40 poly A). The dotted box in FIG. 2B indicates the sequence from pBR322 encoding the origin of replication and β-lactamase (Amp®) gene. CHO cells were transfected with p711 and 6 h later the CMV, Ch1, was introduced to CHO cells previously transfected with p711. Both transfections were performed with lipofectin. The extent of the conversion to the wild-type phenotype was monitored at both biochemical and DNA sequence levels, by spectrophotometric measurement, histochemical staining and analysis of Hirt DNA.

Materials and Methods

Synthesis and purification of oligonucleotides: The chimeric oligonucleotides were synthesized on a 0.2 μmole scale using the 1000 Å wide pore CPG on the ABI 394 DNA/RNA synthesizer. The exocyclic amine groups of DNA phosphoramidites (Applied Biosystems, Foster City, Calif.) are protected with benzoyl for adenine and cytidine and isobutyryl for guanine. The 2'-O-methyl RNA phosphoramidites (Glen Research, Sterling, Va.) are protected with phenoxyacetyl group for adenine, dimethylformamidine for guanine and isobutyryl for cytidine. After the synthesis was complete, the base-protecting groups were removed by heating in ethanol:concentrated ammonium hydroxide (1:3) for 20 h at 55° C. The crude oligonucleotide sample was mixed with 7M urea and 10% glycerol, heated to 70° C. and loaded on a polyacrylamide gel containing 7M urea. After gel electrophoresis, DNA bands were visualized by UV shadowing, dissected from the gel, crushed and eluted overnight in TE buffer (10 mM Tris-HCl and 1 mM EDTA, pH 7.5) with shaking. The eluent containing gel pieces was spun through 0.45 μm spin filter (Millipore, Bedford, Mass.) and precipitated with ethanol. Samples were further desalted by G-25 spin column (Boehringer Mannheim, Indianapolis, Ind.) and greater than 95% of the purified oligonucleotides were found to be full length.

Transient transfection and histochemical staining: CHO cells were maintained in DMEM (B.R.L., Bethesda, Md.) containing 10% FBS (B.R.L. Bethesda, Md.). Transient transfection was carried out by addition of 10 μg of lipofectin in 1 ml of OPTIMEM and added to each well. He alkaline phosphatase activity was measured 24 h after transfection of the oligonucleotide. For histochemical staining, the cells were washed with 0.15M NaCl three times, incubated with staining solution for 20 min and fixed with 50% ethanol. The staining solution consisted of 2 mg Fast Violet, 2 ml Naphtol AS-MX phosphate alkaline solution (Sigma Chemical Company, St. Louis, Mo.) in 50 ml of water.

Spectrophotometric measurement of alkaline phosphate activity: Transient transfection was carried out in triplicates by addition of 1μg of the plasmid p711 with 1 μg of lipofectin in 100 αl of OPTIMEM (B.R.L. Bethesda, Md.) to $1 \times 10^4$ CHO cells in a 96-well place. After 6 h, various amounts of Ch1 or other CMV were mixed with 1 μg of lipofectin in 100 μl of OPTIMEM and added to each well. After 18 h, the medium was aspirated and 200 μl of DMEM containing 10% FBS was added to each well, The alkaline phosphate activity was measured 24 h after transfection of chimeric oligonucleotides. Spectrophotometric measurement was carried out by the Elisa Amplification System (B.R.L. Bethesda, Md.). Cells were washed with 0.15M NaCl three times and lysed in 100 μl of NP40 buffer containing 10 mM NaCl, 0.5% NP40, 3 mM $MgCl_2$ and 10 mM Tris-HCl pH 7.5. A fraction of cell lysates (20 μl) was incubated with 50 μl of Elisa substrate and 50 μl of Elisa amplifier (B.R.L. Bethesda, Md.), the reaction was stopped by addition of 50 μl of 0.3M $H_2SO_4$ after 5 min of incubation with amplifier. The extent of reaction was carried out within the linear range of the detection method. The absorbance was read by an Elisa Plate Reader (B.R.L. Bethesda, Md.) at a wavelength of 490 nm.

Hirt DNA isolation, colony hybridization and direct DNA sequencing of PCR fragment: The cells were harvested for vector DNA isolation by a modified alkaline lysis procedure 24 h after transfection with the chimeric oligonucleotide. The cells were detached by trypsinization, washed, and resuspended in 100 μl of a solution containing 50 mM Tris-HCl pH 8.0, 10 mM EDTA and 110 μl of a solution containing 50 mM Tri-HCl pH 8.0, 10 mM EDTA and 100 μg/ml of RNase A. An equal volume of cell lysis solution (0.2N NaOH and 1% SDS) was added, followed by 100 μl of neutralization solution (3M KAc, pH 5.5). A 10-min room temperature incubation was followed by centrifugation of 10,000 rpm for 10 min. The supernatant was extracted with an equal volume of phenol-chloroform and precipitated with ethanol. Hirt DNA was transformed into *E. coli* DH5α cells (B.R.L. Bethesda, Md.). Colonies from Hirt DNA were screened for specific hybridization for each probe designed to distinguish the point mutation. Colonies were grown on ampicillin plates, lifted onto nitrocellulose filter paper in duplicate, and processed for colony hybridization. The blots were hybridized to $^{32}$P-end-labelled oligonucleotide probes, 711-A (5'-CCGCCTACACCCACTCG-3' (SEQ ID NO: 1)) or 711-G (5'-CCGCCTACGCCCACTCG-3' (SEQ ID NO: 2)) at 37° C. in solution containing 5× Denhardts, 1% SDS, 2× SSC and 100 μg/ml denatured salmon sperm DNA. Blots were washed at 52° C. in TMAC solution (3.0M tetramethylammonium chloride/50 mM Tris-HCl, pH 8.0, 2 mM EDTA and 0.1% SDS). Plasmid DNA was made from twenty colonies shown to hybridize to either 711-G or 711-A, using the Qiagen miniprep kit (Chatworth, Calif.). Several hundred bases flanking the 711 position of each plasmid were sequenced in both direction by automatic sequencing (ABI 373A, Applied Biosystem, Foster City, Calif.). A 190 bp PCR-amplified fragment was generated by Vent$_R$ polymerase (New England Biolabs, Beverly, Mass.) utilizing two primers (5'-CAATGTCCCTGATGTTATGCA-3' (SEQ ID NO: 3) and 5'-CGCTGGGCCAAGGACGCT-3' (SEQ ID NO: 4)), corresponding to position 630–650 and 803–822 of the alkaline phosphatase cDNA flanking the 711 position. The fragment was gel-purified and subjected to automatic DNA sequencing (ABI 373A, Applied Biosystem, Foster City, Calif.).

Oligonucleotide stability measurement: Ten ng of the $^{32}$P-end-labelled oligonucleotide was mixed with 500 ng of the unlabelled oligonucleotide and transfected as described above. In order to reduce a nonspecific binding of oligonucleotides, cells were washed extensively with PBS and a solution containing 1M NaCl/HAc pH 2.5. A crude lysate was prepared by lysing the cells in a solution containing 10 mM Tris-HCl pH 7.5, 0.5 mM MgCl$_2$ and 0.5% Triton x-100 followed by phenol-chloroform extraction. Lysates were analyzed by 15% polyacrylamide gel containing 7M urea followed by autoradiography. Oligonucleotides incubated in DMEM containing 10% FBS were processed and analyzed in the same manner.

In our experimental design, various chimeric oligonucleotides were introduced into CHO cells previously transfected with p711. The extent of the conversion to the wild-type phenotype was monitored by histochemical staining; red pigment was deposited on the cells expressing an active enzyme. When cells with he mutant gene were transfected with Ch1, red cells appeared at a frequency, of approximately one in three transfected CHO cells, on the average, at 11 nM. In contrast, neither Ch2 nor Dh1 caused an increased enzymatic activity. Conversion to wild-type was observed at a low level when cells were transfected with Ch3. The transfection frequency measured by the expression of the wild-type plasmid pHAP was estimated to be 30%.

The enzymatic activity was also measured by spectrophotometric method described above. A dose-dependent increase of alkaline phosphatase activity was observed up to 17 nM of Ch1 in the presence of p711 plasmid. The enzymatic activity of cells treated with Ch1 at 17 nM approached 60% of that observed from cells transfected with the wild-type plasmid, pHAP. The increase was sequence-specific since the same amount of Ch1 did not affect enzymatic activity of cells transfected with pHAP. Furthermore, Ch2 which contained a single base pair change from the Ch1 sequence did not cause any increase in enzymatic activity. The oligonucleotide, Dh1, which contained the same sequence as Ch1, but did not contain a ribonucleotide segment, did not exhibit an increase. Thus, spectrophotometric measurements of alkaline phosphatase activity were consistent with the result from the histochemical staining.

Correction of a point mutation of the targeted DNA sequence by the chimeric oligonucleotide: In order to confirm the change at the DNA sequence level, a Hirt extract was made from the cells transfected with the p711 and various oligonucleotides by a modified alkaline lysis procedure, Wang. G, et al., 1995, Mol. Cell. Biol. 15, 1759, 24 h after transfection of the chimeric oligonucleotide. Hirt DNA transformed DH5α cells efficiently, resulting in 10$^4$ Amp® colonies from 10$^6$ transfected CHO cells. DH5α transformants were screened for specific hybridization with a probe designed to distinguish between the point mutation (A) and the wild-type (G) sequence, corresponding to position 703–719 of mutant and normal cDNAs, respectively, Weiss, M. J., 2988, Proc. Natl. Acad. Sci. 85: 7666. The frequency of correction was measured by averaging the number of colonies hybridized to the 711-G or 711-A probe using more than 500 colonies hybridized to the 711-G or 711-A probe using more than 500 colonies of the multiple plates generated from at least two separate transfection experiments (Table I). Similar frequencies of conversion were observed for two batches of Ch1 prepared by separate synthesis. Approximately 70% of the colonies generated from the Hirt DNA made from cells transfected with p711 and Ch1 hybridized to the 711-A probe, while 30% of colonies exhibited hybridization to the 711-G probe (Table I). Thus, a correction frequency of 30% was observed at 11 nM of Ch1, reproducibly. Hybridization was specific and no cross-hybridization was observed between the two populations. DNA sequencing was carried out with plasmid DNAs prepared from twenty of these colonies in both directions utilizing two primers (5'-CAATGTCCCTGATGTTATGCA-3' (SEQ ID NO: 5) and 5'-CGCTGGGCCAAGGACGCT-3' (SEQ ID NO: 6)), corresponding to position 630–650 and 803–822 of the alkaline phosphatase cDNA flanking the 711 position. The sequence conversion was confirmed in each case and no other alteration in sequence was observed within several hundred of bases surrounding the target nucleotide. All colonies from the Hirt extract prepared from Ch2 or Dh1-treated cells hybridized to the 711-A probe only (Table I). Some colonies from the Hirt extract of the Ch3 hybridized to the wild-type probe, but to a much lesser extent than that of the Ch1 (Table II). These results confirmed that the differential alkaline phosphatase activities exhibited were due to the correction of the point mutation (A to G) at the DNA sequence level.

TABLE II

Hybridization pattern of transformants from Hirt extract prepared from duplicate transfections of the p711 plasmid and various oligonucleotides at 11 nM.

| Oligo-nucleotide | Number of Transfections | Total number of colonies per plate | Number of colonies hybridizing to 711-G | Number of colonies hybridizing to 711-A | % Conversion |
|---|---|---|---|---|---|
| Ch 1 | 1 | 84 | 32 | 54 | 38 |
| | | 189 | 70 | 117 | 37 |
| | | 219 | 74 | 143 | 34 |
| | 2 | 139 | 42 | 98 | 30 |
| | | 162 | 49 | 110 | 30 |
| | | 159 | 51 | 108 | 32 |
| Ch 2 | 1 | 108 | 0 | 108 | 0 |

TABLE II-continued

Hybridization pattern of transformants from Hirt extract prepared from duplicate transfections of the p711 plasmid and various oligonucleotides at 11 nM.

| Oligo-nucleotide | Number of Transfections | Total number of colonies per plate | Number of colonies hybridizing to 711-G | Number of colonies hybridizing to 711-A | % Conversion |
|---|---|---|---|---|---|
|  |  | 90 | 0 | 90 | 0 |
|  | 2 | 218 | 0 | 218 | 0 |
|  |  | 148 | 0 | 148 | 0 |
| Ch 3 | 1 | 190 | 3 | 185 | 2 |
|  |  | 151 | 4 | 145 | 3 |
|  | 2 | 189 | 0 | 185 | 0 |
|  |  | 143 | 0 | 143 | 0 |
| Dh 1 | 1 | 217 | 0 | 217 | 0 |
|  |  | 180 | 0 | 180 | 0 |
|  | 2 | 157 | 0 | 157 | 0 |
|  |  | 188 | 0 | 188 | 0 |

RecA-deficient *E. coli* strains used to propagate plasmid DNA are capable of repair and homologous pairing functions using episomal DNA. In order to rule out the possibility that the sequence conversion is mediated by *E. coli*, direct DNA sequencing of a PCR-amplified fragment of Hirt DNA was carried out. Two primers flanking the 711 position were utilized to generate a 190 bp fragment through the action of Vent$_R$ polymerase. The results indicated that position 711 was a mixture of A(70%) and G(30%) when the Hirt DNA sample was made from the cells transfected cells with the combination of p711 and Ch1. In contrast, no mixed sequence was observed at position 711 when Hirt DNA was made from oligonucleotide Dh1. These results established clearly that sequence correction by the chimeric oligonucleotide occurred in mammalian cells. Stability of chimeric oligonucleotide: The stability of the chimeric oligonucleotide was measured intracellularly and in growth medium containing 10% FBS. Ten nanogram of radiolabelled oligonucleotide, Ch1, was added to the same transfection experiment in which histochemical staining and Hirt DNA analyses was conducted (see Materials and Methods). The chimeric oligonucleotides are extremely stable. No detectable degradation was observed when chimeric oligonucleotide was incubated in growth medium containing 10% FBS, after 24 h incubation. Moreover, oligonucleotide isolated from cells did not exhibit any degradation during the same incubation time. Only monomers of the chimeric oligonucleotide were detected when isolate from cells 24 h after incubation. Thus, under the experimental conditions employed here, no end-to-end litigation of chimeric oligonucleotides was observed.

Example 7.2. The Use of CMV to Mutate the β-Globin Gene in EBV-Transformed Cell Lines A CMV designed to repair the mutation found in Sickle Cell Disease β-globin was designed SC1, FIG. 3. The molecule was composed of DNA residues with two intervening blocks of ten 2'-O-methyl RNA residues flanking a short stretch of five DNA residues. When the molecule was folded into the duplex conformation, one strand contained only DNA residues while the other strand contained the RNA/DNA blocks. In this case, the internal sequence is complementary to the β$^S$ globin sequence over a stretch of 25 residues that span the site of the β$^S$ mutation, with the exception of a single base (T) which is in bold and designated with an asterisk. The five DNA residues flanked by RNA residues were centered about the mutant T residue in the β$^S$ coding sequence. A control chimeric oligonucleotide (SC2) was designed in the same manner with the exception of the base (A) designated in bold and with an asterisk. Genomic sequences of the β$^A$, β$^S$, and closely-related δ-globin genes are also displayed in FIG. 3A with the specific site of β$^S$ mutation printed in bold.

Lymphoblastoid cells were prepared as follows. Heparin-treated blood was obtained from discarded clinical material of a patient with sickle cell disease and from one of the investigators who had neither history nor symptoms of the disease. Mononuclear cells were prepared from blood (=8 ml) by density gradient centrifugation in Ficoll and infected with Epstein-Barr virus which had been propagated in the marmoset cell line 895–8 (Coriell Institute for Medical Research #GM07404D). Infections were performed with addition of 0.1 mg leucoagglutinin PHA-L in 10 ml RPMI medium supplemented with 20% fetal bovine serum in a T25 flask. Cultures were fed twice a week starting on day 5 and were considered established once 60–70% of the cells remained viable at day 21. The β$^A$ and β$^B$ lymphoblastoid cells were maintained in RPMI medium containing 10% fetal bovine serum.

The CMV was introduced into the above-described lymphoblastoid cells homozygous for the is allele as follows. Cells (1×10$^5$ per ml) were seeded in 1 ml of medium in each well of a 24-well tissue culture plate the day prior to the experiment. Transfections were performed by mixing chimeric oligonucleotides with 3 mg of DOTAP (N-[1-(2,3-Dioleoyloxy)propyl]-N,N,N-trimethylammonium methylsulfate, Boehringer-Mannheim) in 20 ml of 20 mM HEPES, pH 7.3, incubated at room temperature for 15 min, and added to the cultured cells. After 6 h the cells were harvested by centrifugation. Washed and prepared for PCR amplification following the procedure of E. S. Kawasaki, PCR Protocols, Eds. M. A. Innis, D. H. Gelfand, J. J. Shinsky and T. J. White, pp146–152, Academic Press, (1990).

Correction of the single base mutation was assessed by taking advantage of well known restriction fragment length polymorphisms resulting from the β$^S$ mutation. R. F. Greeves et al., 1981, Proc. Natl. Acad. Sci. 78: 5081; J. C. Chang and Y. W. Kan, 1982, N. Eng. J. Med. 307: 30; S. H. Orkin et al., ibid., p. 32; J. T. Wilson et al., 1982, Proc. Natl.

Acad. Sci. 79: 3628. The A to T transversion in the β$^S$ allele results in the loss of a Bsu36I restriction site (CCTGAGG). Thus, the β$^S$ allele can be detected by Southern hybridization analysis of genomic DNA cut with Bsu36I. A 1.2 kbp Bsu36I DNA fragment of the β-globin gene present normally is absent in the β$^S$ allele and is replaced by a diagnostic 1.4 kbp fragment. When genomic DNA recovered from homozygous β$^S$ lymphoblastoid cells was analyzed by this procedure, the expected 1.4 kbp fragment was observed. However, two fragments were observed in DNA from cells transfected with the SC1 CMV. The presence of the 1.2 kbp fragment in addition to the 1.4 kbp fragment indicates partial correction of the β$^S$ allele had taken place in a dose-dependent fashion.

To measure the efficiency of correction rapidly and sensitively, we adapted a PCR-based RFLP analysis. For the analysis of the β-globin sequence, the 345 bp PCR fragment was prepared by amplification from a crude cell lysate using primers BG02 (5'-TCCTAAGCCAGTGCCAGAAGA-3' (SEQ ID NO: 7)) and BG05 (5'-CTATTGGTCTCCTTAAACCTG-3' (SEQ ID NO: 8)) and Expand Taq polymerase (Boehringer Mannheim). For the analysis of the β-globin gene, the same cell extracts were used in amplification reactions with primers DG06 (5'-CTCACAAACTAATGAAACCCTGC-3' (SEQ ID NO: 9)) and DG07 (5'-GAAAACAGCCCAAGGGACAG-3' (SEQ ID NO: 10)) to generate a 335 bp fragment. Gels were stained with SYBR™ green (FMC Bioproducts) and fluorescence intensities were quantitated using a Molecular Dynamics fluoroimager. DNA sequencing was performed in both directions using an ABI 373A sequencer.

Figure 4A:
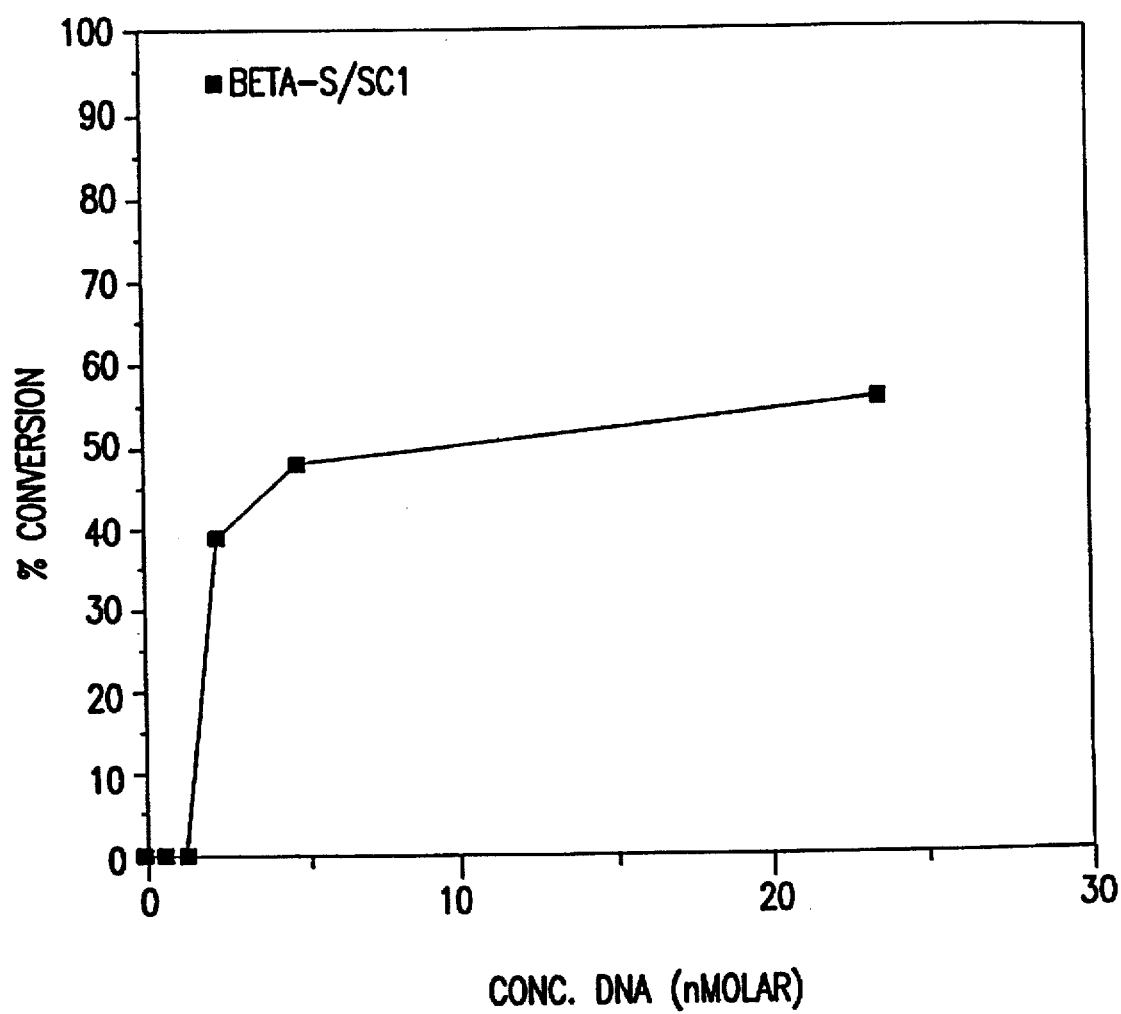
FIG. 4A and 4B.

The above primers were designed to yield a 345 bp fragment spanning the site of the is mutation after PCR amplification of genomic DNA. The fragment from normal cells contained a Bsu36I recognition sequence and yielded fragments of 228 bp and 117 bp, while DNA from is gene contained the sequence CCTGTGG and remained refractory to cutting. Analysis indicated that the 345 bp DNA fragment amplified from SC1-treated is cells was partially cleaved with Bsu36I, indicating correction of the mutation on some, but not all, chromosomes. A quantitative measure was obtained by comparing the relative intensities of the three DNA fragments after electrophoretic separation and staining with the fluorescent dye SYBR™ green. The stained bands were imaged using a laser fluoroimager and the relative levels were calculated. Conversion efficiency was quantitated by scanning the cyber green-stained agarose gel with a fluoroimager. Experiments at doses of between 2.5 and 25.0 pM of SC1/10$^5$ β$^S$ lymphoblastoid cells showed between about 40% and 55% conversion of β$^S$ to β$^A$ (FIG. 4A).

Figure 4B:
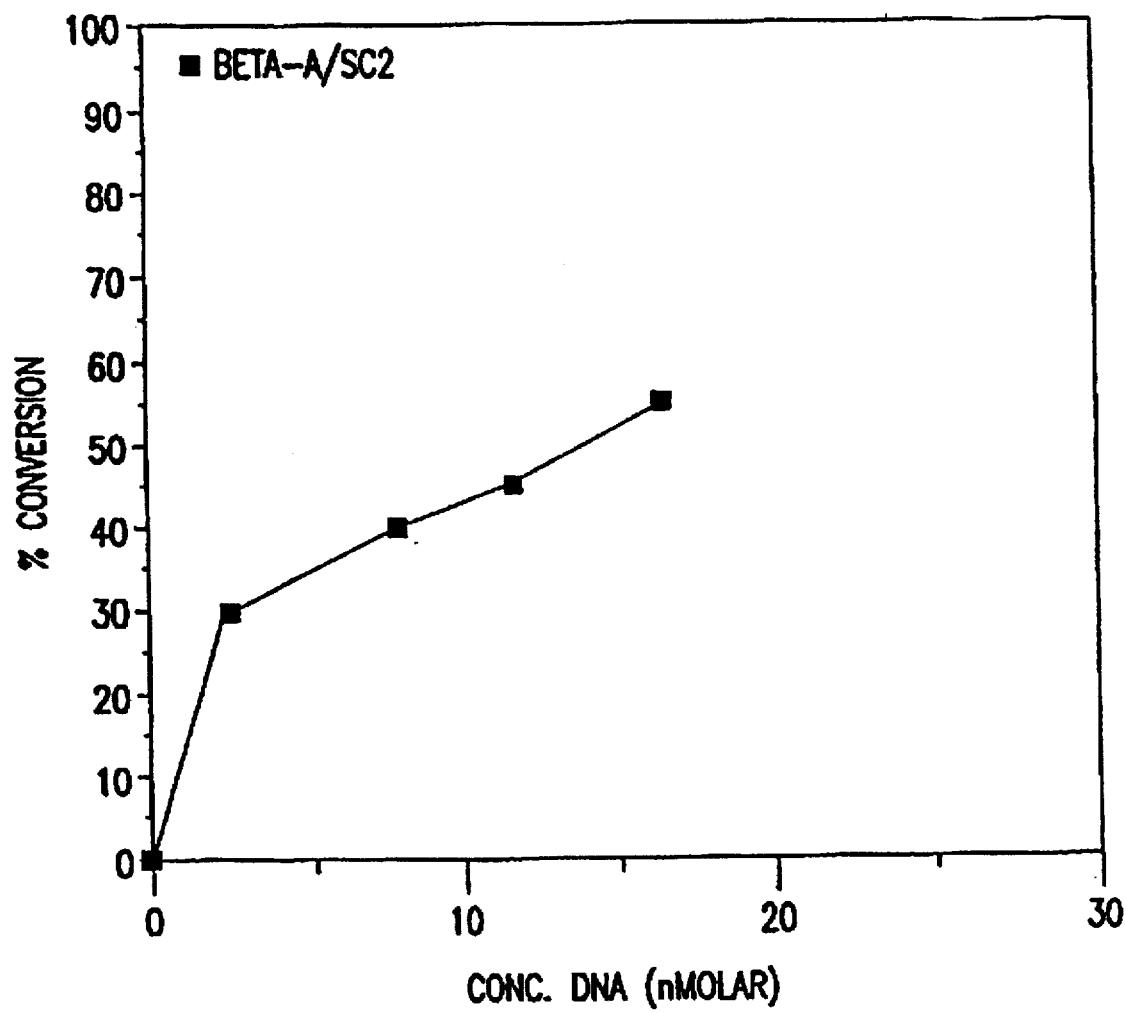

The frequency of introduction of the sickle mutation by the CMV SC2 was also determined by the methods set forth above. Analysis indicated that the level of correction exceeded 50% at the highest level of input chimeric molecule, 25 nM, but even at 2.5 nM correction of 30% of β-globin genes was observed (FIG. 4B).

Direct sequencing of the PCR amplified 345 bp fragment was performed to confirm the T to A change in the coding strand. In the DNA sample from is cells transfected with chimeric molecule SC1 at a higher concentration greater than 12 nM/10$^5$ cells. Sequence analysis revealed an approximately equal mixture of A and T residues at the site of the is mutation. DNA from untreated is cells contained only T at that position and DNA from β$^A$ cells contained only A when treated with SC1. Treatment of is cells transfected with the control CMV SC2 caused no change in the β-globin gene sequence. However, the DNA from normal cells transfected with SC2 was partially converted to the is mutant sequence as evidenced by a mixture of T and A residues at the expected position of the sequence.

The specificity of the action of CMV was assessed by sequencing the related β-globin gene, which is more than 90% homologous to the β-globin gene. The β and δ globin genes are identical over the 5 bp DNA core targeting region of SC1. Two single base differences are underlined in FIG. 3. To determine whether SC2 altered the β-globin gene, DNA sequence analysis was performed as above. The results showed that no alteration was introduced into the δ-globin gene by the SC2 CMV in contrast to the observed change directed by SC2 in the β$^A$-globin sequence.

Example 7.3. The Experimental Use of CMV to Mutate the β-Globin Gene of a HSC

Methods and Materials

Stem cell isolation and transfection: Normal volunteers were given G-CSF 300 μg S.C. twice a day for five days. On the fourth and fifth days of G-CSF therapy they underwent a four hour stem cell apheresis using a COBE spectra pheresis machine. Mononuclear cells were prepared by density gradient centrifugation on Ficoll-Hypaque (density 1.077 g/ml, Pharmacia) (2000 rpm, 10 min, room temperature). The majority of the monocytes were removed after adherence to plastics (30 min, 37° C. in 5% $CO_2$ in RPMI with 10% FBS). Cells were harvested by swirling to remove cells loosely adherent to the plastics which were washed 3 times with PBS. This population was incubated with biotinylated murine anti-CD34 antibodies in PBS/1% BSA for 25 min at room temperature at a concentration of 100×10$^6$ cells/ml. The antibody-treated cells were passed over an avidin column and those passing through the column were then collected for analysis. Subsequently the column was washed with PBS and CD34$^+$ cells adhering to the column were recovered by squeezing the column. Final purities were assessed by FACS.

Cells were re-suspended in RPMI with 10% FCS heat inactivated and 1×10$^5$ cells/ml were plated in a 24 well pate with each well receiving 1×10$^5$ cells. The indicated amounts of chimeric oligonucleotide were mixed with 3 μg DOTAP in 20 μl of 20 mM HEPES, pH 7.3. The mixture was incubated on ice for 15 minutes then added to the cells. After 16 hr at 37° C., 5% $CO_2$, the cells were harvested, pelleted, washed with PBS and lysed with lysis buffer.

PCR Amplification and Analyses: Genomic DNA was amplified for PCR by using PCO$_2$ (5'-TCQTAAGQCAGTGCQAGAAGA-3' (SEQ ID NO: 11) and PCO$_5$ (5'-CTATTGGTCTCCTTAAACCTG-3' (SEQ ID NO: 12)) respectively and Expand Taq polymerase (Boehringer Mannheim, Indianapolis, Ind.) in a 50 μl reaction at 94° C. for 30 sec, 52.5° C. for 30 sec, 72° C. for 30 sec for 35 cycles to generate a 345 bp fragment. For the δ locus, the 5' primer was 5'-CTCACAAACCTAATGAAACCCTGC-3' (SEQ ID NO: 13) and the 3' primer was 5'-GAAAACAGCCCAAGGGACAG-3' (SEQ ID NO: 14) at 94° C. for 30 sec, 59° C. for 30 sec, 72° C. for 30 sec for 35 cycles.

The PCR product was digested with either Dde I or BSU36I restriction endonucleases (New England Biolabs, Beverly, Mass.) and loaded onto 1.2% agarose gel (1×TBE) and electrophoresed. The gel was stained for 20 min in 200 ml of 1×TBE containing 1:20,000 cyber green strain (FMC, Rockland, Me.) in the dark and quantitated by fluoroimager (Molecular Dynamics, Sunnyvale, Calif.). The PCR product was spun through a Qiaquick PCR purification spin column (Qiagen, Chatsworth, Calif.) in $H_2O$, dried down by vacuum to 5 μl and the concentration determined spectroscopically by O.D at 260 nm. The DNA samples (30 μg) were sequenced directly by an automated Applied Biosystems Model 373A DNA sequencing system (Applied Biosystems, Foster City, Calif.).

Synthesis and purification of oligonucleotides: The chimeric oligonucleotides were synthesized on a 0.2 μmole scale using the 1000 Å wide pore CPG on the ABI 394 DNA/RNA synthesizer. In this construct, the exocyclic amine groups of DNA phosphoramidites (Applied Biosystems) are protected with benzoyl for adenine and cytidine and isobutyryl for guanine. The 2'-O-methyl RNA phosphoramidites (Glen Research, Sterling, Va.) are protected with phenoxyacetyl group for adenine, dimethylformamidine for guanine and isobutyryl for cytidine. After synthesis, the base-protecting groups were removed by heating in ethanol: concentrated ammonium hydroxide (1:3) for 20 h at 55° C. The crude oligonucleotides were purified by polyacrylamide gel electrophoresis and the sample was mixed with 7M urea and 10% glycerol, heated to 70° C. and loaded on a 10% polyacrylamide gel containing 7M urea. After gel electrophoresis, DNA bands were visualized by UV shadowing, dissected from the gel, crushed and eluted overnight in TE buffer (10 mM Tris-HCl and 1 mM EDTA, pH 7.5) with shaking. The eluent containing gel pieces was spun through 0.45 μm spin filter (Millipore, Bedford, Mass.) and precipitated with ethanol. Samples were further desalted by G-25 spin column (Boehringer Mannheim) and greater than 95% of the purified oligonucleotides were found to be full length.

RESULTS: The isolated $CD34^+$-enriched population was utilized first in an oligonucleotide uptake experiment. The chimeric molecule SC2 was mixed with the liposome formulation DOTAP under the conditions described above except that a radioactive tag was placed at the 5' end of the oligonucleotide. Increasing amounts of labeled and unlabeled oligonucleotide were incubated with the liposome for 15 minutes. The mixture was then incubated with cells for 6 hours after which the cells were washed extensively with PBS to reduce nonspecific binding. The cells were then centrifuged and the pellet fraction was washed with 0.2M glycine (pH 4.5) to eliminate any remaining nonspecific binding. The radioactivity in the cell pellet was determined by scintillation counting. The chimeric oligonucleotide was absorbed by the cell in dose-dependent fashion. Since our experimental strategy focused on nanomolar concentrations, we did not extend the curve beyond 25 nM. Based on the specific activity of the radiolabelled chimeric oligonucleotide and assuming that each cell is equally receptive to transformation, we estimate that up to approximately 50% of the $CD34^+$ cell population was transfected with the substrate. For each experiment, background levels were assessed by mixing radiolabelled chimeric molecules with the cells in the absence of DOTAP and this level never exceeded 0.05%.

A population of $CD34^+$-enriched cells containing two alleles with $\beta^A$ genotype were transfected with various amounts of SC2 and 3 μg/ml of DOTAP. Genomic DNA was isolated 16 h after transfection as described above and the extent of $\beta^A$ to $\beta^S$ conversion was measured by restriction enzyme polymorphism and by direct DNA sequencing. Genomic DNA isolated from $10^5$ cells was subjected to PCR amplification generating a 345 bp fragment by using the two primers $PCO_2$ and $PCO_5$. The $\beta^A$-specific sequence is cleaved by the restriction enzyme Dde I resulting in three fragments of 192, 108 and 45 base pairs, respectively, while the is-sequence would be cleaved only once, leaving a 300 bp and a 45 bp fragment. An increasing level of the uncut 300 bp fragment was observed as a function of increasing concentrations of SC2, indicating conversion of the $\beta^A$ to $\beta^S$ genotype, FIG. 5. A 50% frequency of conversion was observed at relatively low concentrations of chimeric oligonucleotide (600 ng=30 nM×1 ml). In contrast, no conversion was observed in cells treated with SC1, a chimeric molecule which pairs to the $\beta^A$ site with perfect complementarity.

Figure 5:
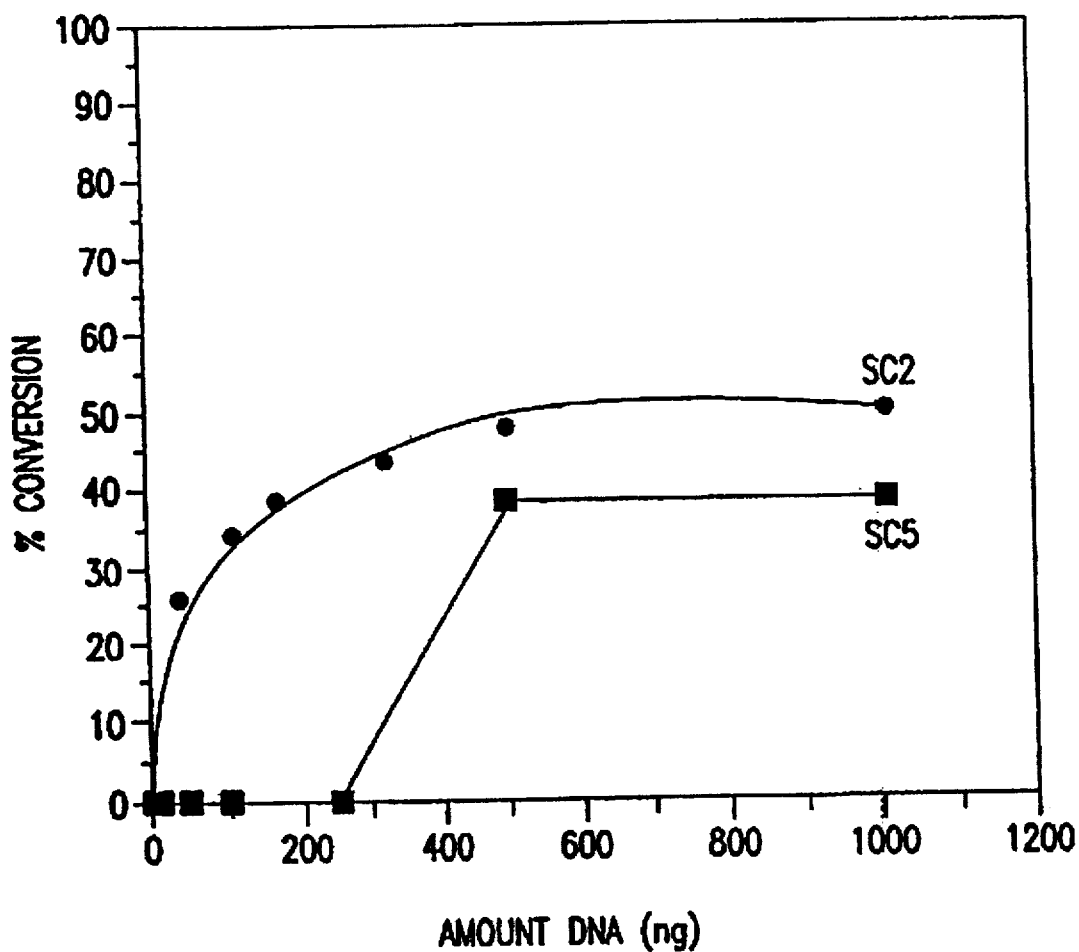
FIG. 5.

In order to confirm the DNA sequence change (A to T) in the normal cells, direct DNA sequencing of the 345 bp-fragment was carried out. The $CD34^+$ population containing homozygous $\beta^A$ alleles was transfected with 23 nM SC2 as described. Genomic DNA was isolated, PCR-amplified and the samples subjected to automated DNA sequencing. The DNA sequence of $\beta^A$ alone and $\beta^A$ treated with the SC1 both contained T. In contrast, the DNA sequence of the $\beta^A$ cells treated with the SC2 showed a dose-dependent conversion of T to A at the expected position. The SC2 CMV contains an (a) segment which is identical to the coding strand of the β-globin gene. The CMV designated SC5 contained an (a) segment identical to a fragment of the non-coding strand of the β-globin gene. We repeated the transfection experiments described above with SC2 and SC5. The results, presented in FIG. 5, show that SC5 was active, though not as active as SC2, and was apparently inactive at concentrations below 20 nM.

Genomic DNA from $\beta^A$ cells that had been treated with SC2 was PCR-amplified utilizing the two β-globin specific primers, $PCO_6$ and $PCO_7$. Only wild-type β-globin sequence was found, which confirmed that the SC2 CMV is β-globin specific.

What is claimed is:

1. An oligonucleobase compound for introducing an alteration in a gene of a eukaryotic cell, which comprises:
   a) a first strand having a 3' end and a 5' end, which first strand comprises:
      1) a total of at least 15 nucleobases;
      2) at least three nuclease resistant ribo-type nucleobases that are selected from the group consisting of 2'AX-nucleosides, 2'AX-nucleotoids, and 2'AR-nucleotides, wherein A=O, F, Cl, or Br and, when A=O, then X=H or $C_{1-6}$ alkane and R=$C_{1-6}$ alkane, and when A≠O, then X and R are omitted; and
      3) at least 3 contiguous ribo-type nucleobases, which can be the same as or in addition to the nuclease resistant ribo-type nucleobases; and
   b) a second strand of nucleobases having a 3' end and a 5' end, wherein the nucleobases of the second strand are Watson-Crick paired to the nucleobases of the first strand, in which the contiguous ribo-type nucleobases of the first strand are Watson-Crick paired to 2'-deoxyribo-type nucleobases.

2. The compound of claim 1, wherein the first strand is a region of an oligonucleobase chain, which chain comprises a 3' and a 5' terminus.

3. The compound of claim 2, in which the first strand comprises at least two segments of at least 3 contiguous ribo-type nucleobases, which ribo-type nucleobases are Watson-Crick base paired to 2'-deoxyribo-type nucleobases.

4. The compound of claim 3, in which each ribo-type nucleobase of the first strand is Watson-Crick paired to a deoxyribo-type nucleobase of the second strand.

5. The compound of claim 4, in which each ribo-type nucleobase of the first strand is selected from the group consisting of 2'AX-nucleosides, 2'AX-nucleotoids, and 2'AR-nucleotides, wherein A=O, F, Cl, or Br and, when A=O, then X=H or $C_{1-6}$ alkane and R=$C_{1-6}$ alkane, and when A≠O, then X and R are omitted.

6. The compound of claim 5, which comprises a first chain having a first 3' terminus and a first 5' terminus, which first chain comprises the first strand, and a second chain, having a second 3' terminus and a second 5' terminus, which comprises the second strand.

7. The compound of claim 6, in which the first and second chains are linked only by Watson-Crick paired nucleobases.

8. The compound of claim 5, which further comprises a region having a sequence of at least 14 contiguous nucleobases or a pair of regions having sequences of at least 7 contiguous nucleobases wherein each said sequence is the sequence of a fragment of a mammalian gene or of its complement.

9. The compound of claim 5, which further comprises a region having a sequence of at least 14 contiguous nucleobases or a pair of regions having sequences of at least 7 nucleobases wherein each said sequence is the sequence of a fragment of a plant gene or of its complement.

10. The compound of claim 5, in which the first strand comprises at least 9 ribo-type nucleobases.

11. The compound of claim 5, in which the second strand contains no ribo-type nucleobases.

12. The compound of claim 5, which contains no peptide nucleobases.

13. The compound of claim 12, which comprises only pentosefuranosyl nucleobases.

14. The compound of claim 13, which comprises one oligonucleobase chain.

15. The compound of claim 14, which further comprises:
   a) a hairpin cap attached to the first strand or the second strand; and
   b) a linker having a first end and a second end, which first end is covalently attached the 3' end of the first strand and which second end is covalently attached to the 5' end of the second strand.

16. The compound of claim 15, in which the 5' end of the first strand is the 5' terminus.

17. The compound of claim 15, in which the 3' end of the second strand is the 3' terminus.

18. The compound of claim 14, which further comprises:
   a) a hairpin cap attached to the first strand or the second strand; and
   b) a linker having a first and a second end, which first end is covalently attached the 5' end of the first strand and which second end is covalently attached to the 3' end of the second strand.

19. The compound of claim 18, in which the 3' end of the first strand is the 3' terminus.

20. The compound of claim 18, in which the 5' end of the second strand is the 5' terminus.

21. The compound of claim 5, in which the first strand comprises a first ribo-segment consisting of at least 6 ribo-type nucleobases, a second ribo-segment consisting of at least 3 ribo-type nucleobases, and an intervening deoxyribo-segment consisting of at least 4 2'-deoxyribo-type nucleobases.

22. The compound of claim 5, in which the first strand comprises a nuclease resistant ribo-type nucleobase other than a 2'OMe-ribonucleotide.

23. The compound of claim 5, in which the second strand comprises a 2'-deoxyribo-type nucleoside or a peptide nucleobase.

24. A method of isolating a cell having an alteration in a target sequence of the genome of the cell, which alteration causes a selectable phenotypic change of the cell, which comprises the steps of:
   a) providing the oligonucleobase of claim 1, which further comprises two regions homologous with a target sequence and a mutator region, disposed there between, encoding the alteration;
   b) maintaining said oligonucleobase within the nucleus of the cell; and
   c) selecting a cell having said selectable phenotypic change.

25. The method of claim 24, wherein the mutator region is 6 or fewer nucleobases.

26. The method of claim 24, wherein the alteration is a deletion of from 6 to one nucleobase.

27. A method of introducing an alteration in a target sequence of the genome of a cultured mammalian cell, which comprises the steps of:
   a) providing the oligonucleobase of claim 8, which further comprises two regions homologous with a target sequence and a mutator region, disposed there between, encoding the alteration; and
   b) maintaining said oligonucleobase within the nucleus of the cell, whereby the alteration is introduced in the target sequence.

28. The method of claim 27, wherein the mutator region is six or fewer nucleobases.

29. The method of claim 27, wherein the alteration is a deletion of from six to one nucleobases.

30. A method of introducing an alteration in a target sequence of the genome of a plant cell, which comprises the steps of:
   a) providing the oligonucleobase of claim 9, which further comprises two regions homologous with a target sequence and a mutator region, disposed there between, encoding the alteration; and
   b) maintaining said oligonucleobase within the nucleus of the cell, whereby the alteration is introduced in the target sequence.

31. The method of claim 30, wherein the mutator region is six or fewer nucleobases.

32. The method of claim 30, wherein the alteration is a deletion of from six to one nucleobases.

* * * * *